United States Patent [19]
Laribiere

[11] Patent Number: 5,501,230
[45] Date of Patent: Mar. 26, 1996

[54] DEVICE FOR PROCESSING BIOLOGICAL SIGNALS SAMPLED BY ELECTRODES ON THE SKIN OF A PATIENT

[75] Inventor: Laurent Laribiere, Montigny, France

[73] Assignee: Commissariat a l'Energie Atomique, Paris, France

[21] Appl. No.: 192,738

[22] Filed: Feb. 7, 1994

[30] Foreign Application Priority Data

Feb. 10, 1993 [FR] France .................................. 93 01462

[51] Int. Cl.$^6$ ............................................. A61B 5/0402
[52] U.S. Cl. ........................... 128/696; 128/734; 607/62; 607/63
[58] Field of Search ................................. 607/62, 63, 2; 128/696, 734

[56] References Cited

U.S. PATENT DOCUMENTS 3,602,215  8/1971  Parnell .
4,174,706  11/1979  Jankelson et al. ..................... 607/62
4,372,319  2/1983  Ichinomiya et al. .................... 607/63
5,146,920  9/1992  Yuuchi et al. ......................... 607/63

FOREIGN PATENT DOCUMENTS 0182197  5/1986  European Pat. Off. .

OTHER PUBLICATIONS

R. McGillivray; "Simple ECG Lead Tester", *Medical & Biological Engineering & Computing*, vol. 29, No. 6, pp. 618–620, Nov. 1991, GB.

*Primary Examiner*—William E. Kamm
*Assistant Examiner*—Kennedy J. Schaetzle
*Attorney, Agent, or Firm*—Burns, Doane, Swecker & Mathis

[57] ABSTRACT

The invention relates to a device for the processing of biological signals sampled by electrodes placed on the skin of a patient, having at least two signal measuring electrodes and a reference electrode, an input differential amplifier (10), whose inputs (11,12) are connected to said two electrodes, and a circuit for detecting the absence of the polarization current of said input differential amplifier (10), so as to supply an alarm signal in the case of a detachment or disconnection of at least one electrode.

8 Claims, 2 Drawing Sheets

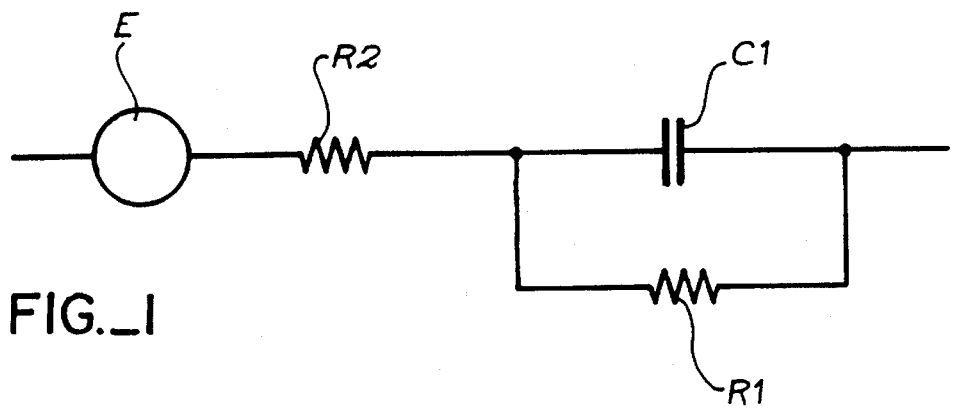
FIG._1
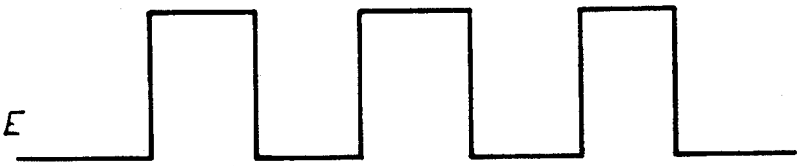
FIG._3A
DCE
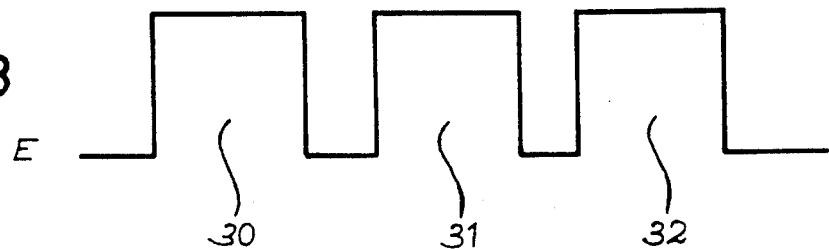
FIG._3B
E
30  31  32

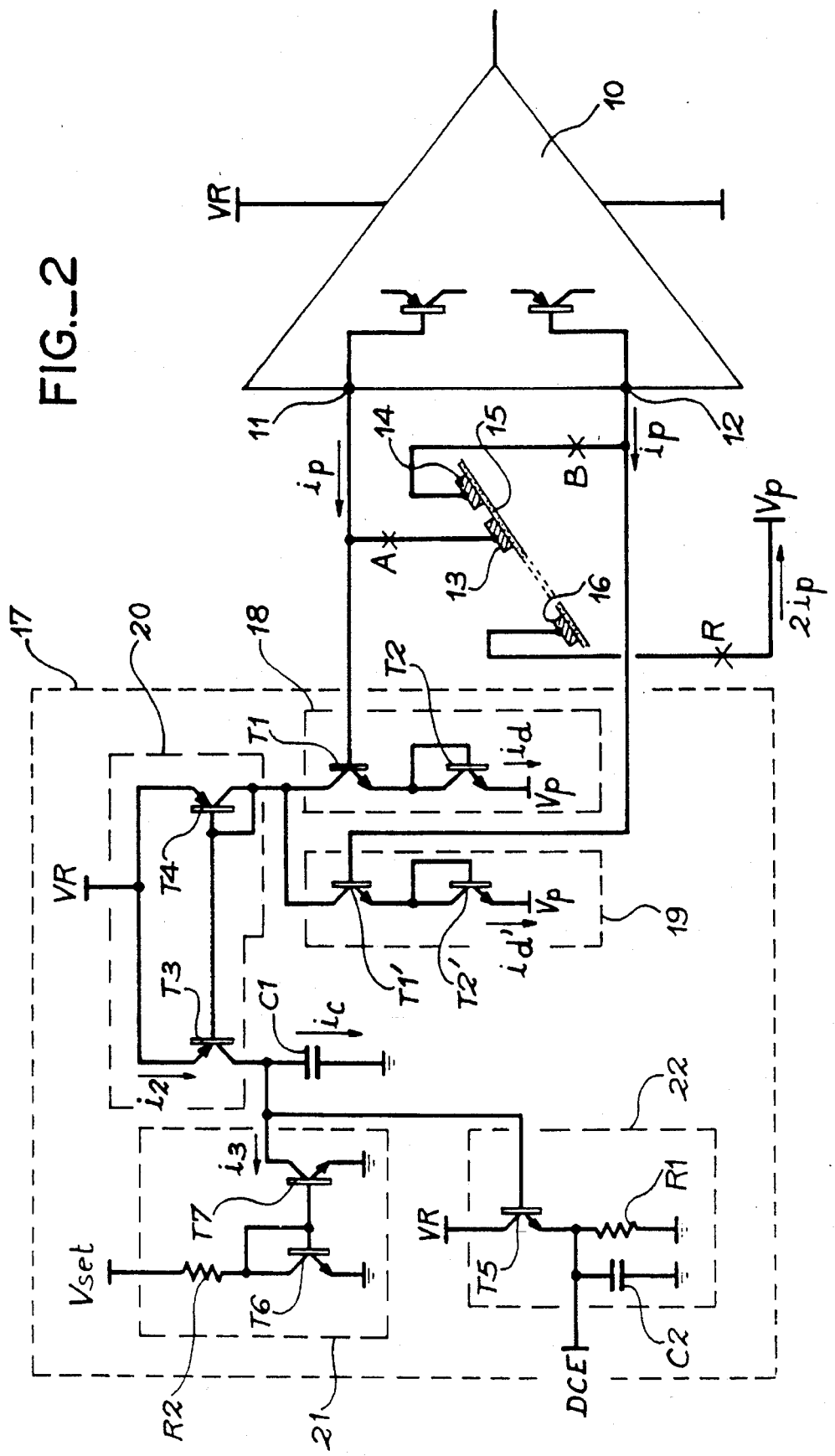
FIG._2

DEVICE FOR PROCESSING BIOLOGICAL SIGNALS SAMPLED BY ELECTRODES ON THE SKIN OF A PATIENT

DESCRIPTION

1. Technical Field

The present invention relates to a device for processing biological signals sampled by electrodes on the skin of a patient.

The invention has applications in the fields of electrocardiography, electroencephalography or any other analysis of biological signals requiring electrodes.

2. Prior Art

Several articles of the prior art relate to such electrode-equipped devices.

An article entitled "Ground-Free ECG Recording with Two Electrodes" by N. V. Thakor, J. G. Webster (IEEE Transactions on Biomedical Engineering, Vol. BME-27, No. 12, December 1980, pp. 699 to 704) describes an electrocardiogram or ECG recording only using two electrodes. Such a recording normally requires three electrodes, the first two being connected to the differential inputs of an ECG amplifier and the third to ground or earth. The two-electrode device makes it possible to improve the safety of the patient by eliminating the ground electrode. A smaller number of electrodes permits easier realization and lower costs.

An article entitled "Electrode Studies for the Long-Term Ambulatory ECG" by N. V. Thakor and J. G. Webster ("Medical and Biological Engineering and Computing", 1985, No. 23, pp. 116 to 121) describes several electrodes developed for use during a long-term ambulatory electrocardiogram, so as to avoid noise and movement defects which interfere with such an ECG recording. This article describes the effects on the defect level of on the one hand a preparation of the skin prior to the positioning of the electrodes and on the other a special configuration and position of the electrodes.

An article entitled "Improved Ag/AgCl Pressure Electrodes" by Y. D. Kingma, N. G. Durdle, J. Lenhart, K. L. Bowes and M. M. Chambers ("Medical and Biological Engineering and Computing", May 1983, pp. 351—357) describes new electrode types making it possible to obtain low impedances at the frequencies used. Such impedances and a limited drift or variation are necessary when the electrodes are used for measuring slow variation signals such as the wave obtained in a gastrointestinal apparatus (0.01 to 10 Hz).

An article entitled "Amplification of Biosignals by Body Potential Driving" by C. L. Levkov ("Medical and Biological Engineering and Computing", March 1982, pp. 248–250) describes a simple circuit having better characteristics than the prior art differential amplifiers.

However, none of these documents is directed at the detection of the interruption or detachment of electrodes placed on a patient subject to an electrocardiogram, encephalogram, or any other analysis requiring a positioning of electrodes.

This detection is fundamental in the case where the patient is under cardiac surveillance. Thus, if the cardiac signal is no longer detected and in the absence of this type of alarm, it is not possible to establish whether the patient is suffering from a cardiac arrest or whether an electrode has become disconnected. The invention aims at a device for the processing of biological signals sampled by electrodes and permitting such a detection.

DESCRIPTION OF THE INVENTION

For this purpose the invention proposes a device for the processing of biological signals sampled by electrodes placed on the skin of a patient having at least two signal measuring electrodes and one reference electrode, and an input differential amplifier whose inputs are connected to said two electrodes, characterized in that the device comprises a circuit for detecting the absence of a polarization current of the input amplifiers, so as to supply an alarm signal in the case of a detachment or disconnection of at least one electrode.

The advantage of this system is that it permits a detection without causing defects and also provides a protection against defibrillation shocks.

Advantageously, the device according to the invention comprises a circuit of the RC type making it possible to eliminate parasitic signals.

In a particularly advantageous embodiment the detection circuit comprises an interruption module connected to two electrodes other than the reference electrode, a current mirror module at the output of said module, a current source module connected to the output of the current mirror module, a capacitor also connected to said same output and a comparison module also connected to said same output and delivering a logic alarm signal.

Each interruption module comprises a first transistor, whose base receives the input signal and the emitter is connected to a second diode-connected transistor, whose emitter is connected to a reference voltage. The current mirror module comprises two current mirror-connected transistors. The current source module comprises a first transistor, whose emitter is grounded and whose base is connected to a second diode-connected transistor, whose emitter is grounded and the collector is connected to a polarization voltage across a resistor.

The comparison module comprises a transistor, whose collector is at a polarization voltage and whose emitter is grounded across a resistor in parallel with a capacitor, the output signal being taken on the emitter of said transistor.

Advantageously, each of the first and second transistors in each of the interruption modules may be replaced with multiple transistors so that the system can absorb more current.

The device according to the invention is particularly suitable for monitoring patients at home.

BRIEF DESCRIPTION OF THE DRAWINGS

FIG. 1 shows an equivalent diagram of an electrode.

FIG. 2 illustrates the device according to the invention.

FIG. 3 illustrates the operation of the device according to the invention.

DETAILED DESCRIPTION OF EMBODIMENTS

According to the invention, the device for processing biological signals sampled by electrodes located at different points on the skin of the patient is such that in normal operation, the patient has a low impedance and the polarization currents of the input amplifier are absorbed by the patient through the electrodes, whilst in the case when an electrode is disconnected, the corresponding polarization current is no longer absorbed by the patient, but instead by the device according to the invention, which amplifies it in order to give an alarm signal.

In such a device, the electrodes are the link between the measurement instrumentation and the biological medium. A distinction can be made between a characteristic impedance of the medium and an interface impedance.

The impedance of the tissues constituting the biological medium has as its electrical equivalent a resistor Rext in parallel with a capacitor Cm in series with a resistor Rin. Rin is the resistance of the intracellular liquid and Rext that of the extracellular liquid, Cm being the capacitance of the membrane. At low frequencies, the current preferably circulates in the extracellular liquid, whereas at high frequencies, the capacitor behaves like a short-circuit, the parallel resistors Rin and Rext representing the equivalent impedance.

The interface impedance is constituted by the impedance between the measuring apparatus and the biological medium. Considering the cable linking the apparatus to the electrode as the constituent of the latter, the interface impedance is then between the electrode/skin impedance or electrode/biological medium impedance. It is broken down into an electrode/electrolyte impedance in series with an electrode impedance.

The electrode impedance is directly linked with the nature of the cable and its length. However, for electrodes used in the frequency range of the electrocardiogram, the capacitive effect of said electrodes is ignored.

The electrode/electrolyte impedance is due to the gel used, which favours the electrode/skin contact. Thus, the skin is constituted by a surface corneous layer and a fatty film covering it, which is the equivalent to a capacitor with a parallel resistor due to the pores, which are more or less conductive channels.

A highly simplified experimental model shown in FIG. 1 can be used for describing the interface impedance, provided that attention is paid to the extreme values which can be assumed by the different constituents. For each electrode, said model comprises an offset voltage E in series with a resistor R2 and a resistor R1 in parallel with a capacitor C1.

The resistor R2 (500 Ω) models the impedance of the cable and the electrode. R1 (1 to 300 K Ω) simulates the electrolyte/skin impedance and that of the biological medium. To take account of the electrode/biological medium capacitive effect, use is made of the capacitor C1 (10 to 300 nF). The offset voltage E (3 mV to 1 V) corresponds to the polarization of the electrodes.

The device according to the invention, as shown in FIG. 2, comprises:

- at least one differential amplifier 10 having its two inputs 11 and 12 connected (points A and B) to two separate electrodes 13,14 placed on the skin 15 of a patient, a reference electrode 16 being placed at another point on the patient's skin;
- a device 17 for detecting the detachment of one of the electrodes comprising:
  - two interruption modules 18 and 19, each having a transistor T1, T'1, whose base receives the input signal, and the emitter is connected to a diode-connected transistor T2, whose emitter is connected to a polarization voltage VP,
  - a current mirror module 20 having two transistors T3 and T4, whose emitters are connected to a polarization voltage VR, the base of the input transistor T4 being connected to its collector at the base of the transistor T3 and to the collectors of the transistors T1 and T'1,
  - a current source module 21 having a transistor T7, whose emitter is grounded, and the base is connected to a diode-connected transistor T6, whose emitter is grounded and the collector is connected to a polarization voltage Vset across a resistor R2, said two transistors T6 and T7 thus being connected in current mirror manner,
  - a capacitor C1 connected to the output of the current mirror module and to the input of the current source module,
  - a comparison module 22 having a transistor T5, whose collector is connected to a voltage VR and whose emitter is grounded across a resistor R1 in parallel with a capacitor C2, the output signal DCE being taken on the emitter of said transistor T5.

In the construction of the device according to the invention shown in FIG. 2, the transistors of the input amplifier and the other transistors are either of the PNP, or of the NPN.

In normal operation, when the electrodes are placed on the patient's skin, the reference voltage VP is at the base of the transistors T1 and T'1. Thus, with each electrode correctly fixed, the polarization current ip flows through the patient (ip=20 nA) and is then absorbed by (VP) to which the patient is connected. The point A or B is then at voltage VP. The transistors T1, T2 and T'1, T'2 are blocked and consequently no current flows in the transistors T4 and T3, which are also blocked. The transistor T3 generates no current in the capacitor C1. Transistor T6 conducts. Transistor T7 generates a current, which leads to the discharge of the capacitor C1 and then the transistor T7 is blocked. The transistor T5 is then blocked and the voltage DCE is 0 volt.

In the case of the detachment of at least one electrode or the breaking of the connection with at least one electrode at point A and/or point B, the polarization current ip is at the base of T1 and/or that of T'1. Said transistor or transistors are conductive. The transistor T4 receiving the base current conducts. This also applies for the transistor T3, which supplies a current to the capacitor C1, which is charged up to the saturation of the transistor T3. The current ic, resulting from the difference of the currents i2 (=id) and I3, charges the capacitor C1 when said difference is not zero. When the charge of C1 is adequate, T5 conducts, producing at the output a logic state close to the voltage VR. The transistors T6 and T7 continue to conduct.

The resistor R1 is made sufficiently high that it does not disturb the charge of C1. The current i3 discharges the capacitor C1 in the absence of detachment. However, this current is sufficiently low to only very partly absorb the current i2, when it exists.

On reconnecting the electrode or electrodes, the transistors T6 and T7 make it possible to obtain a rapid discharge of the capacitor C1.

The capacitor C2 imposes a reaction time on the system, making it possible to eliminate any parasitic signal from the input (pacemaker, defects, etc.). It is possible to obtain the useful information after approximately 1/10 second, which is very adequate in the field in question. If the device has other electrodes, the same structure is then repeated several times.

When the reference electrode is disconnected, no polarization current from other electrodes can be absorbed and then all these currents are detected. Here again, the signal DCE passes to the high state. Thus, equal voltages VA and VB are obtained. The polarization currents ip can no longer pass via the reference electrode. Therefore the transistors T1 and T'1 receive currents on their respective bases, so that there is a return to the preceding problem.

FIG. 3 illustrates the detection of the disconnection of the electrode A (30), the electrode B (31) or the reference electrode (32).

Thus, the device according to the invention absorbs the polarization currents when one or more electrodes are disconnected.

In normal operation (all the electrodes being connected), it is the detection of these currents which indicates abnormal operation. The polarization currents ip of the input amplifier are absorbed by the patient and are collected by the reference electrode. These currents do not traverse the device, because the latter has a much higher impedance than the patient. The output signal (DCE) is then at the low state.

However, when an electrode (13 or 14) is disconnected, the corresponding current ip can only traverse the device, which has a much lower impedance than the disconnected electrode, which is equivalent to an open circuit, i.e. to an infinite impedance. This current is amplified to give the alarm signal DCE, which passes to the high state.

If an electrode (A or B) is disconnected, the device detects a polarization current ip, the other being absorbed by the reference electrode. If the electrodes (A and B) or the reference electrode (R) or ultimately if they are all disconnected, then the device recovers the two polarization currents and triggers the alarm.

Thus, no matter what the case, as a result of recovering the polarization currents or not gives the indication of abnormal operation or not.

The electrode disconnection detection system according to the invention also provides a protection against defibrillation shocks. Thus, the input is protected by series diodes, which are the base junctions of the disconnection detection transistors. So that the system can absorb more current, each of the first and second transistors in each of the interruption modules may be replaced with multiple transistors. An external resistor can also limit said current.

I claim:

1. Device for processing biological signals sampled by electrodes (13, 14, 16) placed on the skin (15) of a patient having at least two signal measuring electrodes (13, 14) and a reference electrode (16), and at least one input differential amplifier (10), whose inputs (11, 12) are connected to said measuring electrodes (13, 14), characterized in that the device comprises a circuit (17) for detecting the absence of a polymerization current of said input differential amplifier (10), and for supplying an alarm signal (DCE) in the case of a disconnection or detachment of at least one measuring electrode.

2. Device according to claim 1, characterized in that it comprises a circuit of the RC type for imposing a reaction time on said alarm signal (DCE).

3. Device according to claim 1, characterized in that the detection circuit (17) comprises an interruption module (18, 19) connected to each of said measuring electrodes (13,14), other than the reference electrode, a current mirror module (20) located at the output of said module (18, 19), a current source module (21) connected to the output of the current mirror module (20), a capacitor (C1) also connected to said same output and a comparison module (22) also connected to said same output and supplying a logic alarm signal.

4. Device according to claim 3, characterized in that said interruption module (18, 19) comprises a first transistor (T1, T'1), whose base receives an input signal and the emitter is connected to a second, diode-connected transistor (T2, T'2), whose emitter is connected to a polarization voltage (VP).

5. Device according to claim 3, characterized in that the current mirror module (20) comprises two current mirror-connected transistors (T3,T4).

6. Device according to claim 3, characterized in that the current source module (21) comprises a first transistor (T7), whose emitter is grounded and the base connected to a second diode-connected transistor (T6), whose emitter is grounded and the collector is applied to a polarization voltage (Vset) across a resistor (R2).

7. Device according to claim 3, characterized in that the comparison module (22) comprises a transistor (T5), whose collector is at a polarization voltage (VR) and the emitter is grounded across a resistor (R1) in parallel with a capacitor (C2), the output signal (DCE) being taken on the emitter of said transistor (T5).

8. Device according to claim 4, characterized in that the interruption module (18, 19) further includes more than one of said first transistor and more than one of said second transistor so that the device can absorb more current.

* * * * *